US010105089B2

(12) United States Patent
Leung et al.

(10) Patent No.: US 10,105,089 B2
(45) Date of Patent: Oct. 23, 2018

(54) SYSTEMS AND METHODS FOR BLOOD PRESSURE MEASUREMENT WITH PSYCHOLOGICAL STATUS VALIDATION

(71) Applicant: Hong Kong Applied Science and Technology Research Institute Co., Ltd., Shatin, New Territories (HK)

(72) Inventors: Lap Wai Lydia Leung, Caseway Bay (HK); Wenbo Gu, Fanling (HK)

(73) Assignee: Hong Kong Applied Science and Technology Research Institute Co., Ltd., Shatin (HK)

( * ) Notice: Subject to any disclaimer, the term of this patent is extended or adjusted under 35 U.S.C. 154(b) by 268 days.

(21) Appl. No.: 14/933,647

(22) Filed: Nov. 5, 2015

(65) Prior Publication Data

US 2016/0100787 A1    Apr. 14, 2016

Related U.S. Application Data

(63) Continuation-in-part of application No. 14/307,503, filed on Jun. 18, 2014, now Pat. No. 9,931,076.

(51) Int. Cl.
*A61B 5/16* (2006.01)
*A61B 5/00* (2006.01)
(Continued)

(52) U.S. Cl.
CPC ............ *A61B 5/165* (2013.01); *A61B 5/0064* (2013.01); *A61B 5/0082* (2013.01);
(Continued)

(58) Field of Classification Search
CPC ... A61B 5/165; A61B 5/7296; A61B 5/02405; A61B 5/02116; A61B 5/7221; A61B 5/0064; A61B 5/0082; A61B 5/489
See application file for complete search history.

(56) References Cited

U.S. PATENT DOCUMENTS 6,050,951 A    4/2000  Friedman et al.
8,187,196 B2   5/2012  Amitzur et al.
(Continued)

FOREIGN PATENT DOCUMENTS

WO    WO 2009/138923    * 11/2009    ............... A61B 5/04

OTHER PUBLICATIONS

Lantelme, et al. "White Coat Effect and Reactivity to Stress." American Heart Association. Apr. 1998. pp. 1021-1029.*

*Primary Examiner* — Tiffany Weston
(74) *Attorney, Agent, or Firm* — Norton Rose Fulbright US LLP

(57) ABSTRACT

Techniques for effectively and accurately measuring psychological influencing factors, such as the white coat effect and mental stress, that may affect or otherwise influence biometric measurements, such as blood pressure measurements, are described. Embodiments of a measurement validation system herein may utilize a method for determining an artery location on a living subject's skin and positioning a tonometry pressure sensor on the artery location for tonometric blood pressure measurement to obtain pressure pulse data for a subject. In operation according to embodiments, measurement logic of a measurement validation system may utilize the pressure pulse data to extract blood pressure data, heart rate data, blood pressure variability data, and heart rate variability data. The foregoing data may be utilized in identifying whether the blood pressure measurement properly and accurately reflects the situation of the subject.

21 Claims, 12 Drawing Sheets

(51) Int. Cl.
*A61B 5/021* (2006.01)
*A61B 5/024* (2006.01)

(52) U.S. Cl.
CPC ...... *A61B 5/02116* (2013.01); *A61B 5/02405* (2013.01); *A61B 5/489* (2013.01); *A61B 5/7221* (2013.01); *A61B 5/7296* (2013.01)

(56) References Cited

U.S. PATENT DOCUMENTS

| | | | |
|---|---|---|---|
| 2005/0228297 A1* | 10/2005 | Banet | A61B 5/021 600/485 |
| 2008/0081963 A1 | 4/2008 | Naghavi et al. | |
| 2009/0124914 A1 | 5/2009 | Kuo et al. | |
| 2009/0326391 A1 | 12/2009 | Chan et al. | |
| 2012/0316448 A1* | 12/2012 | Gu | A61B 5/02108 600/499 |
| 2013/0158417 A1 | 6/2013 | Borger | |

* cited by examiner

SYSTEMS AND METHODS FOR BLOOD PRESSURE MEASUREMENT WITH PSYCHOLOGICAL STATUS VALIDATION

CROSS-REFERENCE TO RELATED APPLICATIONS

The present application is a continuation-in-part of U.S. patent application Ser. No. 14/307,503 entitled "METHOD AND DEVICE FOR TONOMETRIC BLOOD PRESSURE MEASUREMENT," filed Jun. 18, 2014, the disclosure of which is hereby incorporated herein by reference.

TECHNICAL FIELD

The invention relates generally to blood pressure measurement and, more particularly, to blood pressure measurement with psychological status validation.

BACKGROUND OF THE INVENTION

Tonometric blood pressure measurements is a non-invasive means for continuously monitoring blood pressure (BP) and obtaining additional cardiovascular parameters such as arterial stiffness, cardiac output and stroke volume. Before making such measurement, an accurate position of an artery location is required to be identified over a person's skin.

It is possible to use a single pressure sensor to search for the artery location when the sensor presses on the skin, as in U.S. Pat. No. 8,597,195. During the search, a constant hold-down pressure exerted by the sensor on the skin is required to be maintained. Due to the curvature of a body part under measurement, such as a wrist of a person, the sensor is required to finely and dynamically adjust its position to keep a constant hold-down pressure during the search. A long search time is usually resulted. U.S. Pat. No. 7,771,361 and US20100286538 suggest using an array of optical and pressure sensors to press on the skin to thereby identify the artery location. Although the search time is shorter, accuracy of the artery location is limited by the sensor dimension. High accuracy is achievable only with a small sensor size, the implementation of which is costly.

In obtaining blood pressure measurements, such as through the use of the aforementioned tonometric sensor means, a link between the doctor taking such measurements and higher blood pressure readings has been identified. This link is known as the "white coat effect" or "white coat hypertension" (WCH). The white coat effect, which is believed to be the result of subjects being more nervous when examined by a physician, results in a measured difference above 20 mm Hg in systole and/or 10 mm Hg in diastole over the subject's blood pressure measurement without influence of the effect. Accordingly, it is important to identify whether blood pressure measurement data properly and accurately reflects the situation of the subject and is not affected by phenomena such as the white coat effect.

Techniques for profiling cardiovascular vulnerability to mental stress have been attempted in the art. For example, United States patent application publication number US2008/0081963 describes a method for profiling an individual's vulnerability to detrimental effects of mental stress on vascular function. The disclosed method utilizes a cuff blood pressure sensor for measuring blood pressure at one location on the individual's body and a photoplethysmography (PPG) sensor for measuring blood flow data at a different location on the individual's body, and thus does not provide data which is directly and precisely coupled to the blood pressure data (i.e., the measured data is decoupled in sensed location). Moreover, due to the blood pressure cuff restricting the blood flow during blood pressure measurement, the PPG sensor is unable to measure blood flow data simultaneously with the blood pressure measurement, thereby also decoupling the measured data in time (i.e., decoupled in sensed time). In operation, the method monitors changes in the mental stress levels and changes in the vascular function levels in the individual during a mental stress challenge and correlates the changes of mental stress levels with the changes in vascular function levels to profile the individual's vulnerability to detrimental effects of mental stress on vascular function. The technique does not, however, operate to identify whether blood pressure measurement data properly and accurately reflects the situation of the subject and is not affected by phenomena such as the white coat effect, but instead merely correlates the effect of mental stress with blood pressure.

Other techniques have attempted to monitor variations in the physiological index to initiate blood pressure measurement. For example, United States patent application publication number US2013/0158417 describes a method for non-invasively determining blood pressure by deriving a physiological index from an individual, wherein the physiological index is indicative of a sympathetic activity in the individual, monitoring variations in the physiological index, and instructing a blood pressure determination unit to initiate blood pressure determination when the variations meet a predetermined condition. The method utilizes a PPG sensor at one location on the individual's body and ECG sensors at other locations on the individual's body for measuring heart rate data and a blood pressure sensor located at still another location on the individual's body for measuring blood pressure data, and thus the measured data is decoupled in sensed location. In operation, the method initiates the blood pressure measurement after determining that the monitored variations in the physiological index meet the predetermined condition, thus decoupling the measurements in sensed time. This technique, like the above described technique, does not operate to identify whether blood pressure measurement data properly and accurately reflects the situation of the subject and is not affected by phenomena such as the white coat effect, instead controlling blood pressure measurement in response to certain monitored variations in the physiological index.

Still other techniques have attempted to determine endothelial dependent vasoactivity. For example, U.S. Pat. No. 8,187,196 describes a system having a plurality of sensors disposed at different locations on an individual to extract a pulse-wave time parameter from the signals provided by the sensors. A spectral analyzer of the system then analyzes the pulse-wave time parameter to derive a frequency decomposition which is representative of the endothelial dependent vasoactivity of the individual. As with the methods described above, the described technique does not operate to identify whether blood pressure measurement data properly and accurately reflects the situation of the subject and is not effected by phenomena such as the white coat effect, instead controlling blood pressure measurement in response to certain monitored variations in the physiological index.

BRIEF SUMMARY OF THE INVENTION

An aspect of the present invention is a method for determining an artery location on a living subject's skin and positioning a tonometry pressure sensor on the artery location. In the method, a non-contact optical search and a contact pressure search are performed. An optical-sensing unit having a light source and an optical detector is employed in a non-contact process to scan the skin along a scan path thereon in order to determine a search region within the scan path. The search region is determined such that an artery is predicted to lie thereunder. The artery location is then searched within the search region by a contact-based process of sweeping the pressure sensor along the search region.

The non-contact process further determines a height profile characterizing the scan path's curvature. The sweeping of the pressure sensor is guided by curvature information provided by the height profile.

In the non-contact process, the optical-sensing unit progressively scans the skin along the scan path with a light beam generated by the light source and configured for blood sensing while the optical detector measures an instantaneous power level of the light beam reflected from the skin and a body section thereunder so that a time sequence of the measured power levels is obtained after the scanning is done. The search region is searched and identified within the scan path according to the time sequence of the measured power levels. During the scanning, the optical-sensing unit's position is controlled to maintain a pre-determined distance between the unit and the scan path for eliminating a nuisance factor in obtaining the time sequence of the measured power levels. After the scanning is done, a time history of the unit's coordinates is obtained and the height profile is derived therefrom.

During the scanning of the skin, preferably an instantaneous distance of the light source from the scan path is estimated by one or more selected instantaneous power levels that have been measured so as to feedback-control the unit's position to maintain the pre-determined distance between the unit and the scan path.

In the contact-based process, the pressure sensor is positioned onto the search region with a hold-down pressure to be within a pre-determined pressure range. A first initial coordinate of the search region for the pressure sensor to directly move to is determined according to the height profile, thereby allowing the hold-down pressure to be attained by fine-positioning the pressure sensor around the first initial coordinate. The pressure sensor then progressively sweeps along the search region to measure a pressure pulse amplitude generated by the artery so that a sequence of measured amplitudes is obtained after the sweeping is done. During the sweeping, plural second initial coordinates of the search region for the pressure sensor to move to are determined according to the height profile. Within the search region, the artery location is determined from the obtained sequence of measured amplitudes to thereby allow the pressure sensor to be positioned on the artery location for blood pressure measurement.

A tonometric BP monitoring device is realizable by including a pressure sensor, a light source and an optical detector, and by configuring the device to determine an artery location and position the pressure sensor thereon according to the method disclosed herein.

An aspect of the present invention provides techniques for effectively and accurately measuring psychological influencing factors, such as the white coat effect and mental stress, that may affect or otherwise influence biometric measurements, such as blood pressure measurements. For example, embodiments of a measurement validation system herein may utilize embodiments of the above described pressure sensor to obtain pressure pulse data for a subject. In operation according to embodiments, measurement logic of a measurement validation system may utilize the pressure pulse data to extract blood pressure data, heart rate data, blood pressure variability data, and heart rate variability data, wherein all such data is derived according to embodiments herein from measurements taken from the same location on the subject at the same time (i.e., collection of different metrics are neither staggered in time nor gathered from different positions on the subject's body). The foregoing data may be utilized according to embodiments in identifying whether the blood pressure measurement properly and accurately reflects the situation of the subject. For example, analysis logic of a measurement validation system may compare heart rate variability data and blood pressure variability data with baseline data for the subject in determining the validity of the blood pressure data (e.g., determining whether the blood pressure data is or is not effected by one or more psychological influencing factors, such as the white coat effect and mental stress).

Other aspects of the present invention are disclosed as illustrated by the embodiments hereinafter.

DETAILED DESCRIPTION OF THE INVENTION

As used herein in the specification and appended claims, "a DC component" of a plurality of data is an average value of the data. It is also used herein that "an AC component" of a sequence of original data is a sequence of computed data each of which is an original data minus the DC component of the sequence of original data.

If a single pressure sensor is used in searching for an artery location over a person's skin, a pre-determined hold-down pressure exerted by the sensor on the skin is required to be maintained by fine-adjusting the sensor's position. The non-flat curvature of the skin necessitates the pressure sensor to test a lot of fine positions in verifying if the desired hold-down pressure is exerted, thereby significantly increasing the search time. The present invention achieves a reduced search time by decomposing the search into a first stage of determining a search region by a non-contact optical search for coarsely identifying an artery location, and a second stage of contact pressure search for finely identifying the artery location within the search region. Testing whether a desired hold-down pressure is exerted is required only in the second stage. To further reduce the search time, the first stage maps the curvature of the skin, and the resultant map is used in the second stage to enable a pressure sensor to quickly land on the skin and to follow the skin's curvature during scanning the search region so that the number of times in fine-positioning the pressure sensor for hold-down pressure verification is minimized.

An aspect of the present invention is to provide a method for determining an artery location on a living subject's skin and positioning a tonometry pressure sensor on the artery location for measuring BP of the living subject. The living subject can be a person and, as in many instances of medical examination, the artery location to be searched may be confined to an area of the skin on a hand or a wrist of the person. However, the present invention is not limited only to a human wrist in locating an artery. The present invention is applicable for other parts of a human body such as a neck. The living subject may also be an animal such as a horse.

Figure 1:
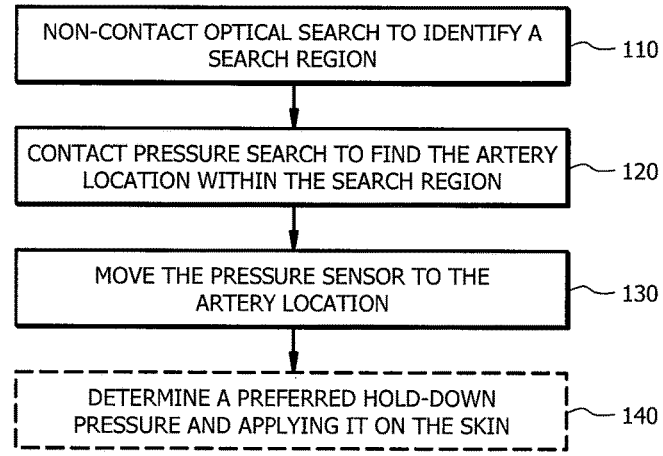
FIG. 1 depicts the steps in an exemplary method of the present invention.
Figure 3:
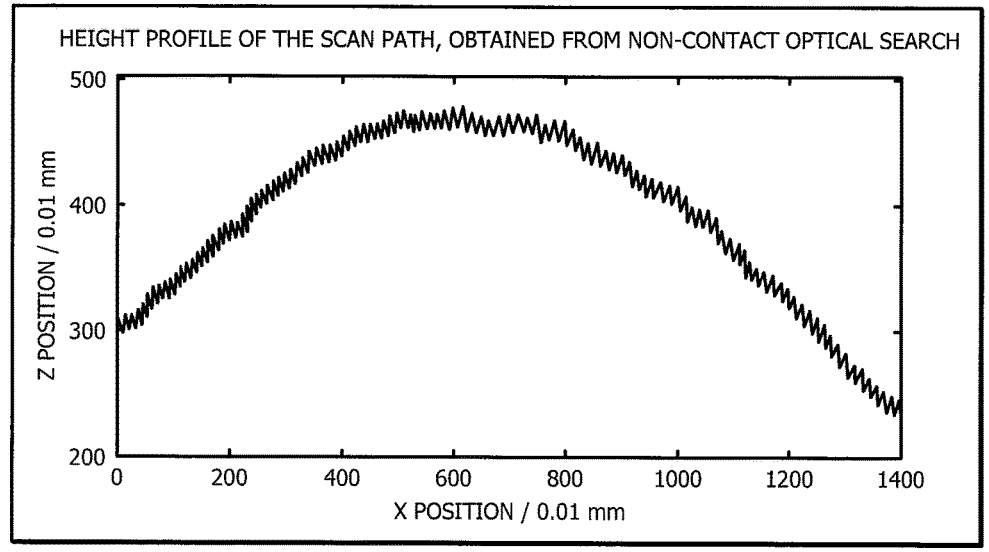
FIG. 3 is an example of a height profile obtained from the non-contact optical search.

Exemplarily, the method is illustrated with the steps thereof depicted in FIG. 1. The method employs an optical-sensing unit having a light source and an optical detector. The method comprises a non-contact optical search followed by a contact pressure search. A non-contact process 110 of using the optical-sensing unit to scan the skin along a scan path on the skin is first performed in order to determine a search region within the scan path. The search region is determined such that an artery is predicted to lie thereunder. The non-contact process 110 further determines a height profile of the scan path. The height profile is a map obtained in mapping the scan path's curvature, and characterizes a distance-height relationship along the scan path. In one form, the height profile is represented as a set of coordinates describing the skin's two-dimensional geometric positions along the scan path. An example of such height profile is shown in FIG. 3. After the non-contact process 110 is done, the artery location is searched within the search region by a contact-based process 120 of sweeping the pressure sensor along the search region. The sweeping is guided by curvature information provided by the height profile. That is, the height profile provides a next location's coordinate for the pressure sensor to move to during the sweeping such that the pressure sensor closely follows the skin's curvature in the sweeping. Note that the non-contact process 110 and the contact-based process 120 are for the non-contact optical search and the contact pressure search, respectively, mentioned above. Afterwards, the pressure sensor is moved to and positioned on the artery location, as in a step 130, for doing BP measurement, which may be preceded by a step 140 of determining a preferred hold-down pressure and applying it to the skin.

Figure 2:
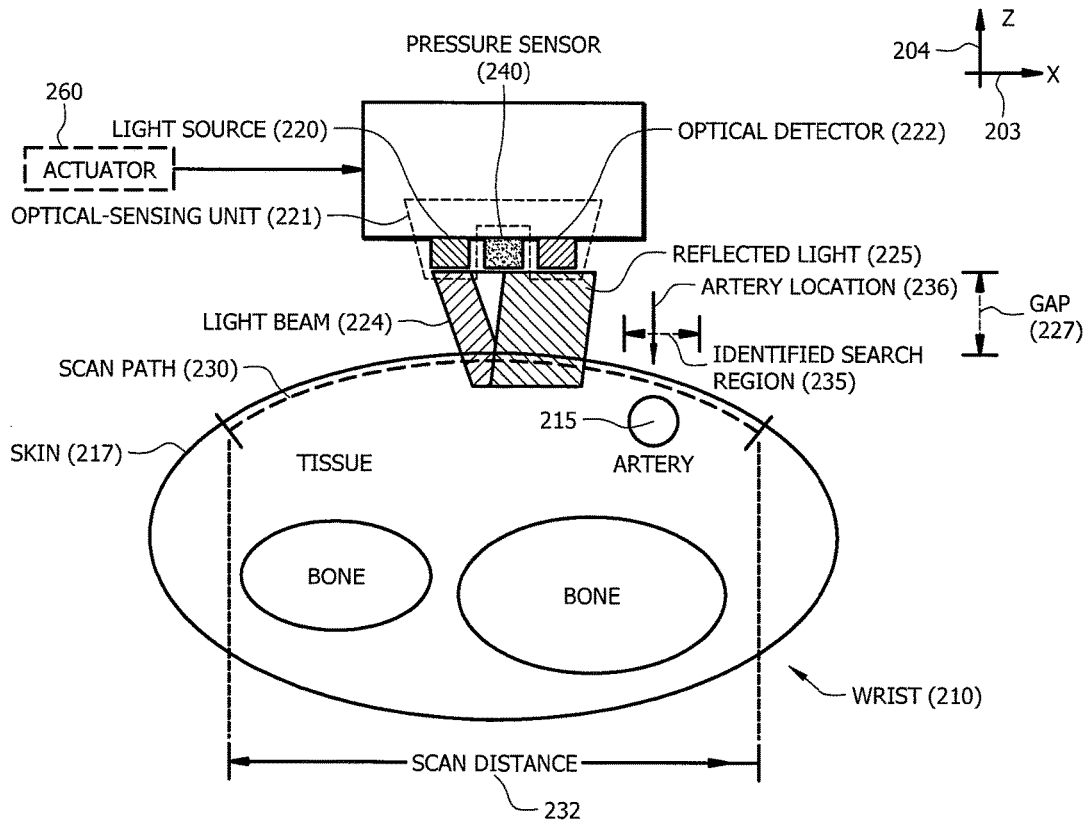
FIG. 2 depicts an arrangement of identifying an artery location according to the exemplary method of the present invention.

The two processes 110, 120 are exemplarily illustrated with an aid of FIG. 2, which shows an arrangement for identifying an artery location 236. For illustration purpose, a wrist 210 is considered in searching for an artery 215 therein; the present invention is not limited to identifying an artery location on a human wrist only.

In the non-contact process 110, an optical-sensing unit 221 comprising a light source 220 and an optical detector 222 progressively scans a living subject's skin 217 along a scan path 230 thereon with a light beam 224 generated by the light source 220 and configured for blood sensing while the optical detector 222 measures an instantaneous power level of reflected light 225, which is a part of the light beam 224 reflected from the skin 217 and a body section thereunder. Preferably the light beam 224 comprises an infrared light component responsive to the presence of blood by optical absorption. After the scanning is done, a time sequence of measured power levels is obtained, from which a search region 235 within the scan path 230 is identified.

In practical implementation, the scanning is usually done along an X-direction 203, i.e. a reference horizontal direction. For the human wrist 210, a straight-line scan distance 232 between 15 mm to 20 mm measured in the X-direction 203 is usually sufficient for the scanning of the scan path 230 in order to search for the artery 215, which generally has a diameter of 2 mm to 3 mm. Despite this size of the artery 215, an effective measurement range is only around 0.5 mm.

As is mentioned above, the accuracy of identifying the artery location 236 by an optical sensor is determined by its size. To avoid a need for an ultra-small optical sensor, practically the search region 235 may be set with a length of 3 mm to 4 mm. Preferably the light beam 224 is a collimated one with a beam size not greater than 2 mm if a search length of 3 mm to 4 mm is selected.

Due to non-contact scanning, there is a gap 227 between the optical-sensing unit 221 and the skin 217. Note that the instantaneous power level measured at the optical detector 222 is affected by the length of the gap 227. If such length varies during the scanning, this fluctuation causes a nuisance factor in obtaining the measured power levels, making analysis of the resultant time sequence difficult. Hence, during the scanning, it is required to control the position of the optical-sensing unit 221 to maintain a pre-determined distance, measured in a Z-direction 204, i.e. in a reference vertical direction, between the unit 221 and the scan path 230 for eliminating the nuisance factor. In one embodiment, the pre-determined distance is selected between 1 mm to 2 mm. An additional advantage of maintaining this distance is that after the scanning is done, a time history of coordinates traveled by the unit 221 is obtained and a height profile of the scan path 230 can be derived therefrom.

The optical-sensing unit 221 can be controlled to maintain the pre-determined distance from the skin 217 by, for example, first using a laser-based technique to measure the length of the gap 227. Despite this, an implementation cost is reducible by using the optical-sensing unit 221 to measure the length of the gap 227 in addition to identifying the search region 235. It is first noticed that body materials that absorb the light beam 224 include blood, tissue and bone, and that pulses of blood travel through the artery 215 at different time constants. It is also noted that motion of the blood pulses causes a time-varying component, i.e. an AC component, in the time sequence of measured power levels. Removing this AC component from the time sequence gives a DC component, which is determined by tissue, bone, and non-pulsing blood flowing in veins, as well as by the length of the gap 227. As the skin reflection dominates the DC component and it attenuates quickly with the increase of gap length, the length of the gap 227 can be estimated by the DC component.

It follows that maintaining the pre-determined distance between the optical-sensing unit 221 and the scan path 230 is achievable by, during the scanning of the skin 217, estimating an instantaneous distance of the light source 220 from the scan path 230 by one or more selected instantaneous power levels that have been measured and then using the estimated instantaneous distance in a feedback control loop to adjust the unit 221's position. Preferably, the instantaneous distance is estimated according to a DC component computed from the one or more selected instantaneous power levels.

In maintaining the pre-determined distance for the gap 127 by the feedback control loop, the time history of coordinates traveled by the unit 221 is recorded. FIG. 3 shows an example of the height profile computed from this time history, which is in turn obtained according to the instantaneous distances computed from the aforementioned DC components.

Figure 4:
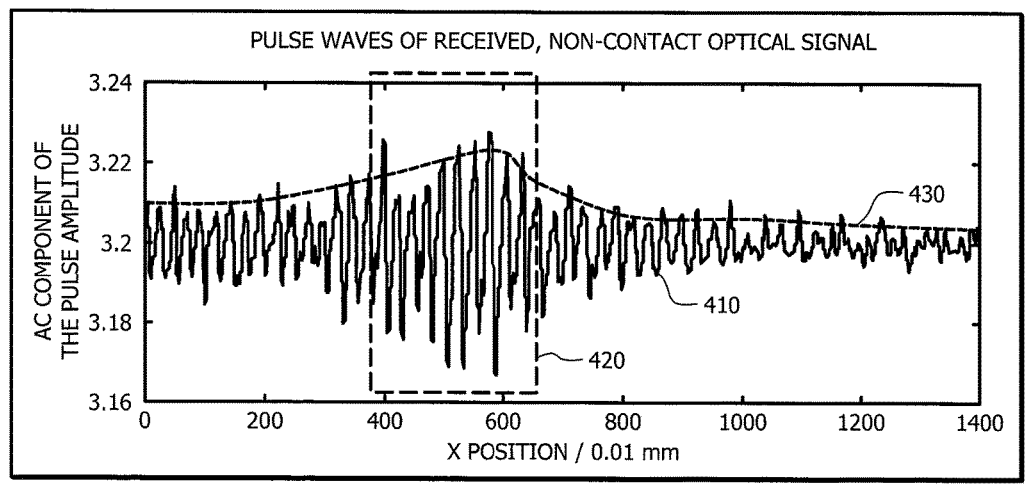
FIG. 4 is an example showing an AC component of pulse amplitude detected by an optical detector, indicating how the artery location is identifiable from the AC component.

FIG. 4 shows an example of identifying a search region 420 through computing AC components of a sequence 410 of measured power levels. The fluctuation in the AC components over positions along the X-direction 203 is due to pulsing of blood through the artery 215. An envelope 430 is computable from the sequence 410. The search region 420 is selected to be a window of −3 mm enclosing the greatest amplitude in the envelope 430.

In the contact-based process 120, a pressure sensor 240 is moved in the Z-direction 204 and is positioned onto the search region 235 with a hold-down pressure set within a pre-determined pressure range. This pressure range may be set as a small range around a nominal value. The nominal value is a desired value of the hold-down pressure. This desired value may be a value selected from 30 mmHg to 100 mmHg in general. For example, the desired value may be set at 50 mmHg. The small range around the nominal value is a tolerance level within which a small variation of the hold-down pressure exerted by the pressure sensor 240 is permissible. An XZ coordinate that the pressure sensor 240 lands on or directly moves to the search region 235 is termed a first initial coordinate and is determined by the height profile. Then the hold-down pressure can be attained by fine-positioning the pressure sensor 240 along the Z-direction 204 around this initial coordinate. Afterwards, the pressure sensor 240 is driven to progressively sweep along the search region 235 to measure a pressure pulse amplitude generated by the artery 215. A sequence of measured amplitudes is obtained after the sweeping is done. During the sweeping along the search region 235, plural XZ coordinates for the pressure sensor 240 to move to are determined according to the height profile, these XZ coordinates being termed second initial coordinates. Within the search region 235, the artery location 236 is determined from the obtained sequence of measured amplitudes.

Figure 5:
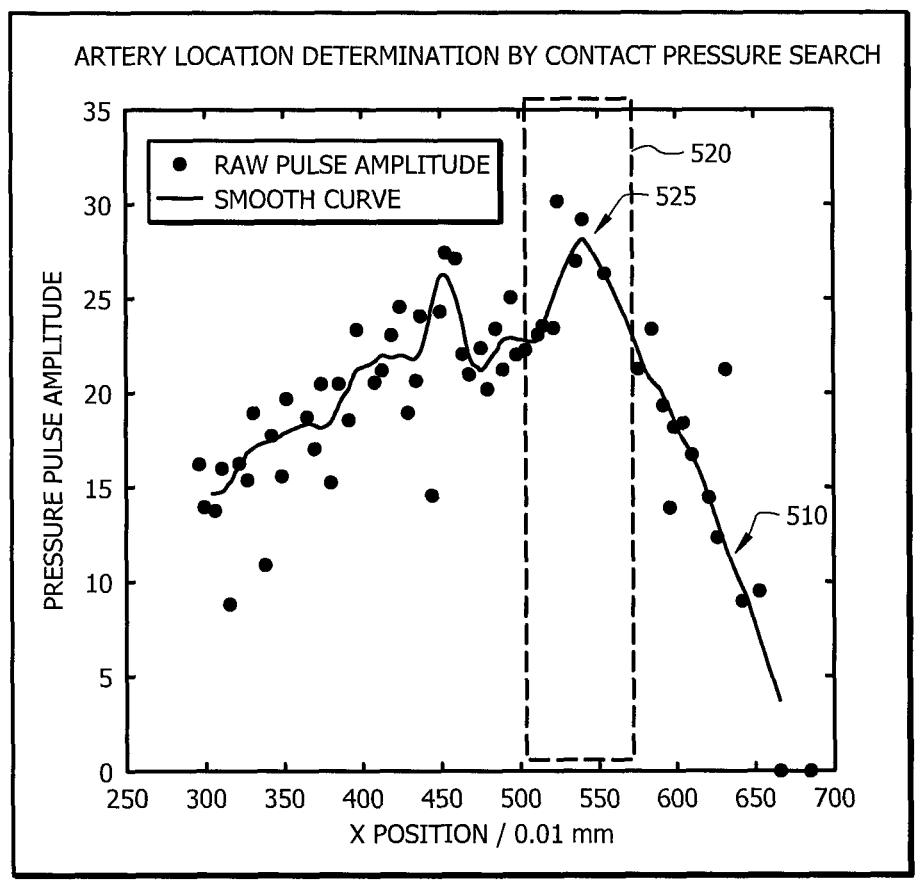
FIG. 5 is an example of determining the artery location from raw data obtained in a contact pressure search.

In one approach shown in FIG. 5, raw data of measured amplitudes are processed by a curve fitting method to from a smooth line 510, from which a maximum point 525 is identified. Since the pressure sensor 240 may not be able to be positioned exactly on the X-position of the maximum point 525 due to implementation constraints, the artery location 236 may be a location selected from a window 520 of −0.5 mm (the effective measurement range mentioned above) enclosing the maximum point 525.

Figure 6:
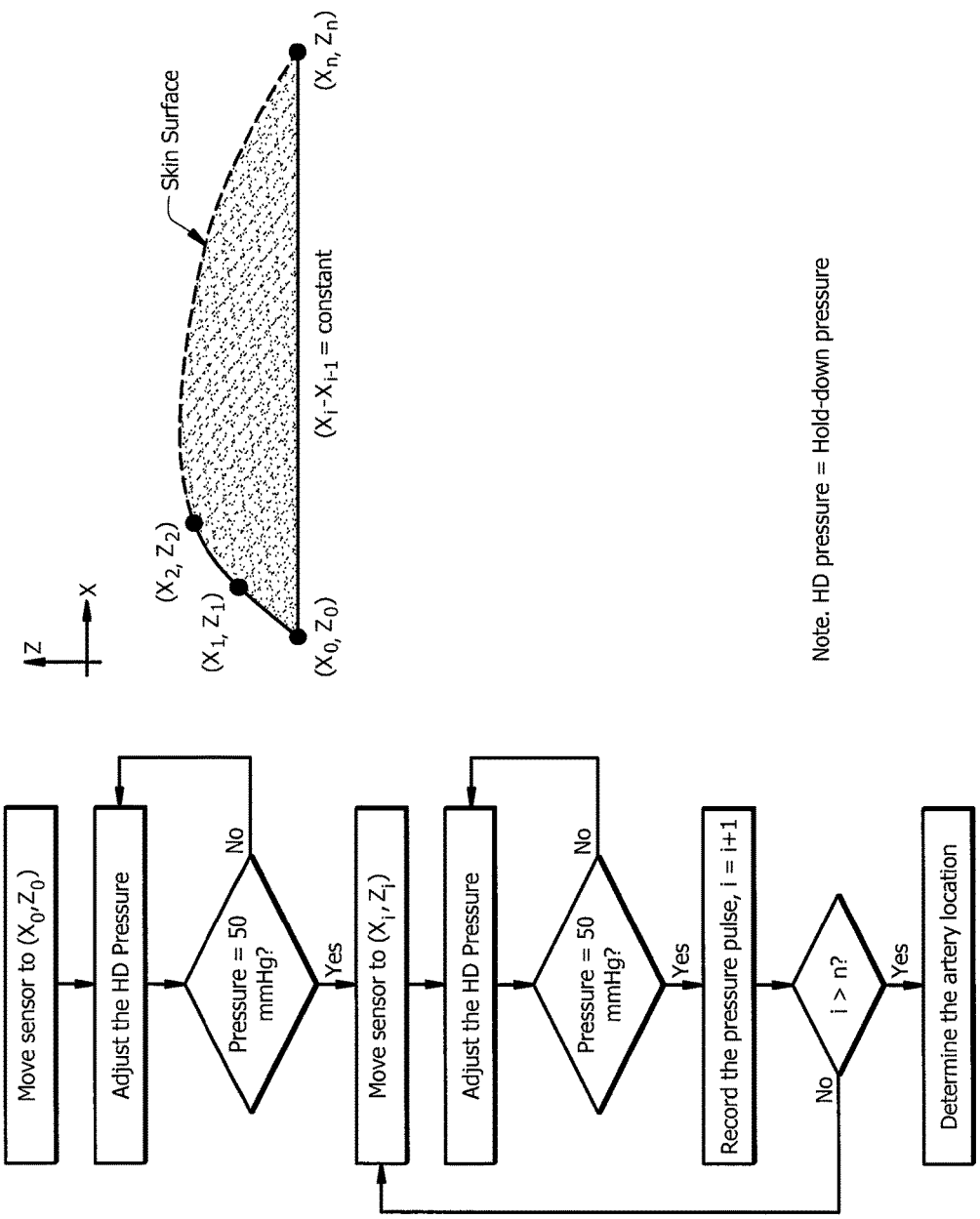
FIG. 6 provides a first flowchart as one example for illustrating how the artery location is determined by the contact pressure search.

FIG. 6 is an example illustrating how the artery location 236 is determined by the contact-based process 120. During the sweeping of the pressure sensor 240 along the search region 235, the pressure sensor 240's position is finely adjusted in the Z-direction 204 to maintain the hold-down pressure to be within the pre-determined pressure range when the pressure sensor 240 reaches any of the second initial coordinates, such as $(X_1, Z_1)$, $(X_2, Z_2)$ and $(X_n, Z_n)$ in FIG. 6.

Figure 7:
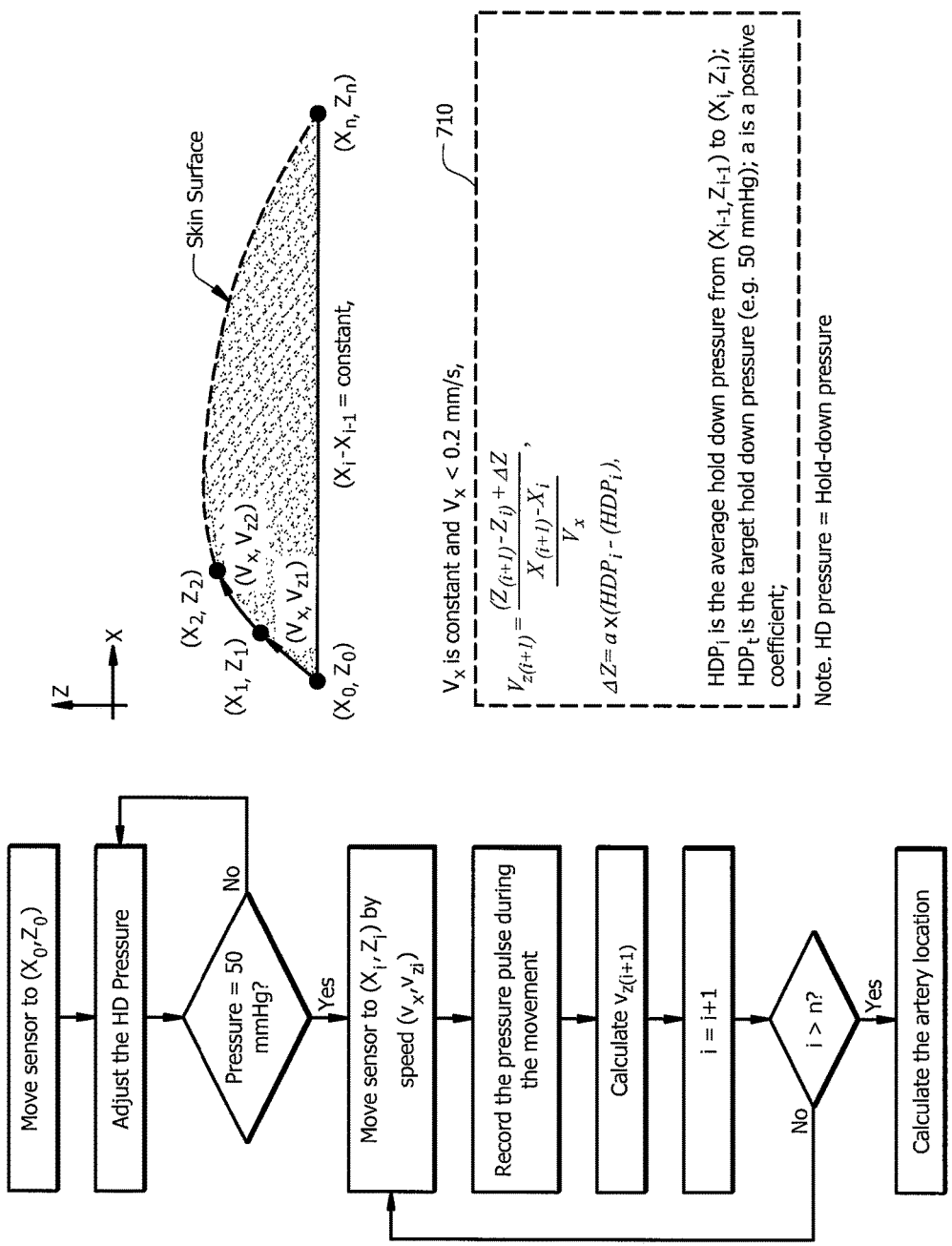
FIG. 7 provides a second flowchart as another example of the artery-location determination in the contact pressure search.

FIG. 7 gives another example of the contact-based process 120. Different from the one shown in FIG. 6, the hold-down pressure is not checked upon moving to any of the second initial coordinates. An algorithm 710, mentioned herein as an example, is employed to adjust the values of measured amplitudes for compensation of a variation in the hold-down pressure.

Figure 8:
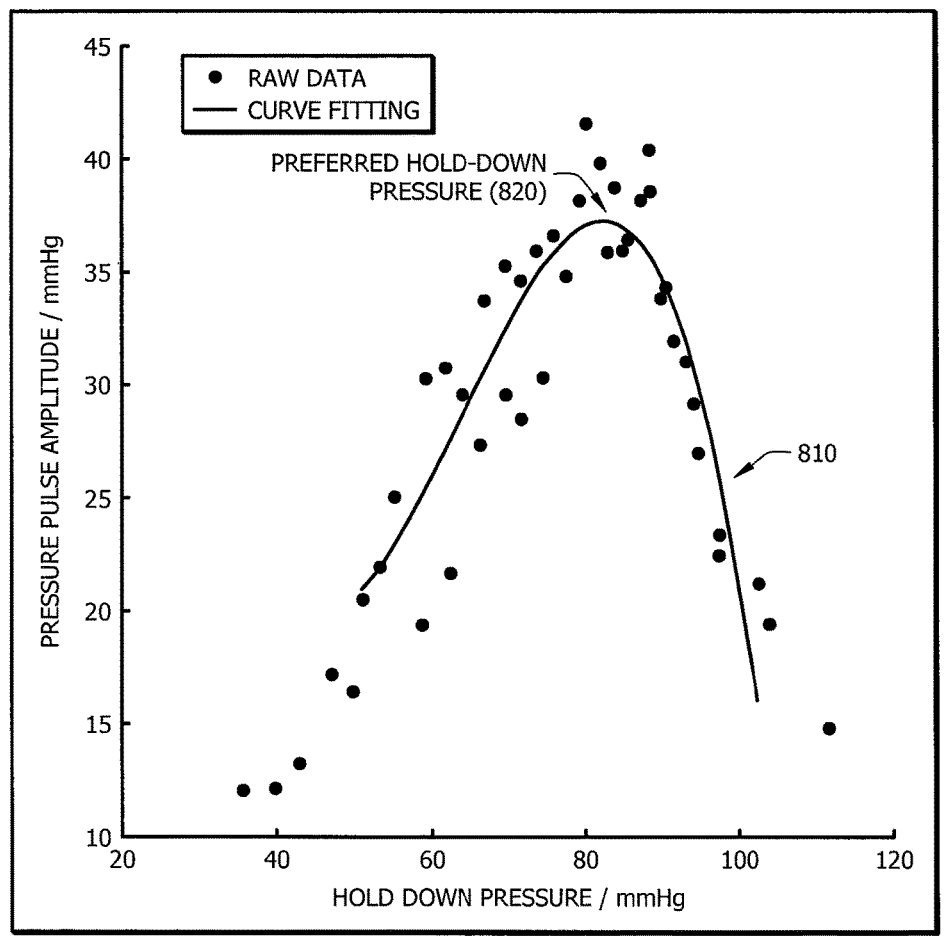
FIG. 8 is an example indicating how a preferred value of hold-down pressure is determined after the artery location is identified.

After the artery location 236 is determined and the pressure sensor 240 is positioned thereon, an optimization step, which is the optional step 140 mentioned above, can be performed by determining a preferred value of the hold-down pressure and exerting this preferred pressure value on the artery location 236. This optimization step is made by progressively increasing or decreasing the hold-down pressure while the pressure sensor 240 measures pressure pulse amplitudes at plural time instants. One approach for computing the preferred pressure value is illustrated with an aid of FIG. 8. In FIG. 8, raw data of the pressure pulse amplitudes give a smooth curve 810 by a curve-fitting technique. A maximum point 820 identified in the curve 810 is the preferred pressure value. After the preferred value is obtained, the pressure sensor 240 is fine-positioned in the Z-direction 204 so as to exert this preferred value on the artery location 236.

As shown in FIG. 2, the pressure sensor 240 and the optical-sensing unit 221 may be arranged to from one single integrated unit such that one actuator 260 is usable to move the single integrated unit in both the reference horizontal direction (the X-direction 203) and the reference vertical direction (the Z-direction 204). Alternatively, the pressure sensor 240 and the optical-sensing unit 221 may be implemented as separate units so that an actuating arrangement comprising plural actuators is used. Alternatively, the pressure sensor 240, the optical-sensing unit 221 and the actuator 260 may be integrated as one single unit and be able to move in both the reference horizontal direction (the X-direction 203) and the reference vertical direction (the Z-direction 204).

It is apparent that a tonometric BP monitoring device for measuring BP of a living subject is realizable by including a pressure sensor, a light source and an optical detector, and by configuring the device to determine an artery location on the living subject's skin and position the pressure sensor on the artery location according to the method disclosed herein.

Embodiments of the present invention provide operation to effectively and accurately measure psychological influencing factors that may affect or otherwise influence biometric measurements, such as the foregoing blood pressure measurements. For example, embodiments of the invention are operable to identify the presence of a psychological influencing factor, such as the white coat effect and mental stress. In operation, the aforementioned pressure sensor 240, placed in juxtaposition with artery 215 as described above, may be utilized in measuring a subject's blood pressure. However, the subject's blood pressure may be affected by one or more psychological influencing factor, thereby rendering the blood pressure measurement inaccurate or unrepresentative of the subject's true physiological state. Accordingly, a measurement validation system adapted according to the concepts herein is provided according to embodiments to identify when one or more such psychological influencing factor is present which may be affecting a measurement. In order to effectively and accurately ensure detection of a psychological influencing factor is coupled to, and thus likely affecting, the measurement, embodiments utilize a same sensor at a same time as that used for the measurement being validated (i.e., coupled in sensed time and in sensed location).

Figure 9:
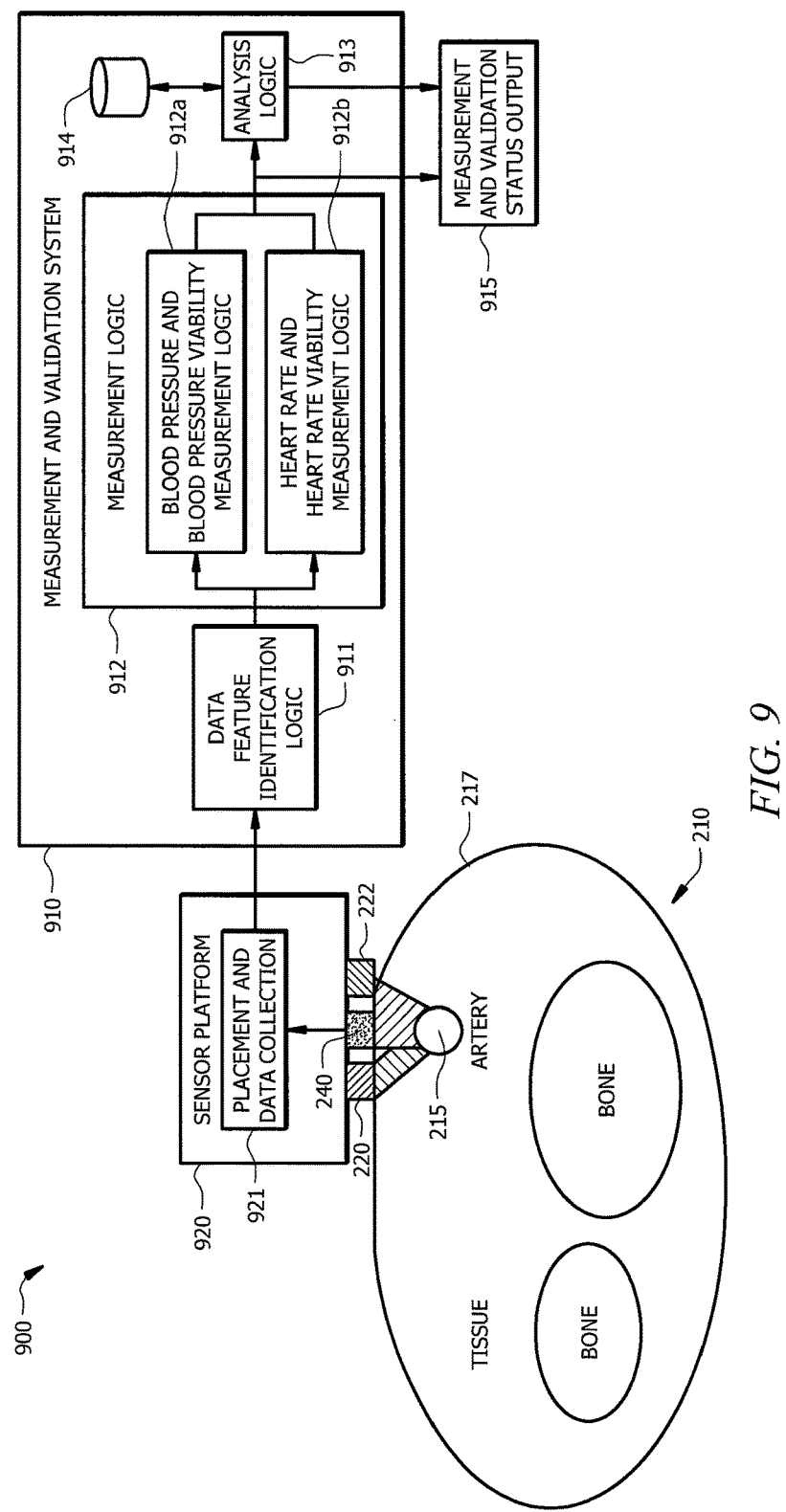
FIG. 9 shows a system operable to provide psychological status validation with respect to biometric measurements according to embodiments of the invention.

FIG. 9 shows an embodiment of a system operable to provide psychological status validation with respect to biometric measurements as psychological status validation system 900. Psychological status validation system 900 illustrated in FIG. 9 includes the sensor platform of FIG. 2 adapted to measure psychological influencing factors according to embodiments of the present invention. Sensor platform 920 (including light source 220, optical detector 222, and pressure sensor 240 described above) is shown positioned to place pressure sensor 240 in position (e.g., in contact with the skin of a subject with a predetermined hold-down pressure as described above) for continuously collecting blood pressure data. For example, placement and data collection logic 921 may have controlled one or more actuator to position the sensor platform using the non-contact optical search for coarsely identifying an artery location and the second stage of contact pressure search for finely identifying the artery location, in accordance with embodiments described above. Thereafter, data collection logic 921 may collect data as utilized herein from pressure sensor 240 (e.g., receive signals from pressure sensor 240, possibly filtering or otherwise processing signals, such as to aggregate signals, digitize signals, transform signals, etc., for further processing by additional functionality). Such data may be provided to measurement and validation system 910 (e.g., as raw data, filtered data, digitized data, or otherwise processed data, etc.) for determining and/or reporting the measured blood pressure. In operation according to embodiments, data feature identification logic 911, measurement logic 912, and analysis logic 913 utilize data provided by data collection logic 921 to measure one or more biometric attribute and to identify when one or more psychological influencing factor is present and may be affecting a measurement.

Figure 10:
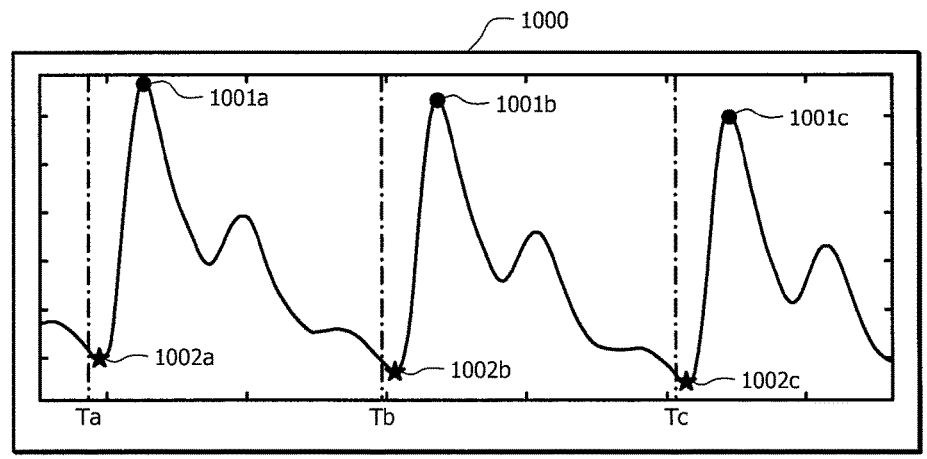
FIG. 10 shows an example of a pressure pulse signal as may be utilized by a psychological status validation system of embodiments of the invention.

FIG. 10 shows an example of three cycles (referred to herein pressure waveforms) of a pressure pulse signal (shown as signal 1000) as may be provided by pressure sensor 240. It should be appreciated that pressure pulse signal 1000 may be provided by pressure sensor 240 in the unit of voltage (V). Data collection logic 921, data feature identification logic 911, measurement logic 912, and/or analysis logic 913 may operate to transform pressure pulse signal 1000 to one or more other unit of measure for measurement and/or validation operation according to the concepts herein.

Blood pressure logic 912a of measurement logic 912 may, for example, operate to transform pressure pulse signal 1000 from voltage values to absolute pressure values (e.g., mmHg values) according to the calibration results of pressure sensor 240 and/or measured subject. Thus, in operation according to embodiments, continuous blood pressure values (BP) may be presented as BP=a*V+b, wherein the coefficient a may be determined by the sensitivity of pressure sensor 240 and the tissue effect of measured subject and the coefficient b may be determined by the tissue effect of measured subject. Blood pressure logic 912a of embodiments may operate to determine the systolic and diastolic blood pressure (SBP and DBP) using the values of pressure pulse peaks (e.g., pressure peaks 1001a, 1001b, 1001c, etc.) and troughs (pressure troughs 1002a, 1002b, 1002c, etc.) respectively.

Through continual monitoring of the pressure sensor signal, measurement and validation system 910 may determine the heart rate. For example, data feature identification logic 911 of embodiments may operate to identify the peaks and/or troughs and/or feature points in the pressure waveforms of a pressure pulse signal provided by data collection logic 921. Heart rate logic 912b of measurement and validation system 910 of embodiments may operate to use the pressure peaks (e.g., pressure peaks 1001a, 1001b, 1001c, etc. of the pressure waveforms) detected in the signal over a period of time to determine the subject's heart rate. For example, pressure peaks 1001a, 1001b, and 1001c may be detected in time t1, t2, and t3 as shown in FIG. 10, whereby the time intervals of the first and second heart cycles may be determined as t2-t1 and t342, respectively. The heart rate may be determined from the inverse of the time interval of heart cycle. Additionally or alternatively, the heart rate may be calculated according to the time intervals of pressure pulse troughs (pressure troughs 1002a, 1002b, 1002c, etc. of the pressure waveforms) or any other periodic feature points of pressure pulse signal 1000. Any or all such data may be provided by measurement and validation system 910 to analysis logic 913 and/or output 915 for facilitating operation as described herein.

Measurement and validation system 910 of the embodiment illustrated in FIG. 9 is coupled to output 915 to provide blood pressure measurement validation data thereto. For example, when operation of measurement and validation system 910 determines that a psychological influencing factor is present that may be affecting or otherwise influencing the blood pressure measurement, a signal indicating invalidity of the measurement may be provided to output 915 (e.g., to cause output 915 to suppress reporting of the blood pressure measurement, to report a warning or other doubtful designator with the blood pressure measurement, to trigger one or more additional blood pressure measurements, etc.). Alternatively, when operation of measurement and validation system 910 determines that a psychological influencing factor is not affecting or otherwise influencing the blood pressure measurement, a signal indicating validity of the measurement may be provided to output 915 (e.g., to allow output 915 to report the blood pressure measurement, to report an approval or other reliable designator with the blood pressure measurement, to cause the blood pressure measurement to be recorded, such as in a database used in establishing baseline metrics for the subject, etc.).

Psychological influencing factors may be measured or otherwise identified according to embodiments of the invention using blood pressure variability data and heart rate variability data. The table below generally illustrates the correspondence between blood pressure variability, heart rate variability, and heart rate to the white coat effect and mental stress experienced by a subject. For example, the presence of mental stress may be accompanied by the subject's heart rate variability being below a baseline heart rate variability for the subject. As a further example, the presence of white coat effect may be accompanied by the subject's blood pressure variability being above a baseline blood pressure variability for the subject and the subject's heart rate variability being above a baseline heart rate variability for the subject.

| Psychological Influencing Factor | Blood Pressure Variability (BPV) | Heart Rate Variability (HRV) | Heart Rate (HR) |
| --- | --- | --- | --- |
| White Coat Effect | ↑ | ↑ | — |
| Mental Stress | ↑ | ↓ | ↑ |

Measurement and validation system 910 of the illustrated embodiment comprises data feature identification logic 911, measurement logic 912, and analysis logic 913, wherein measurement logic 912 of the illustrated embodiment includes blood pressure logic 912a and heart rate logic 912b. In operation according to embodiments, measurement logic 912 may utilize data obtained from pressure sensor 240 (e.g., as provided by placement and data collection logic 921) to derive or extract a suite of data to be utilized by analysis logic 913 to measure psychological influencing factors determining and/or to determine that a psychological influencing factor is present that may be affecting or otherwise influencing a measurement being made, such as a blood pressure measurement. In operation according to embodiments, pressure pulse data is provided to measurement logic 911 (e.g., the pressure pulse signal provided by pressure sensor 240 and/or pressure peak and pressure trough data provided by data feature identification logic 911) for measuring one or more biometric attribute and identifying when one or more psychological influencing factor is present and may be affecting a measurement. Such pressure pulse data is used by blood pressure logic 912a of embodiments to extract not only blood pressure data (e.g., as described above), but also to extract blood pressure variability data (described in further detail below). Likewise, such pressure pulse data is used by heart rate logic 912b of embodiments to extract not only heart rate data (e.g., as described above), but also to extract heart rate variability data. Using the same pressure pulse data from which the blood pressure measurement is made to also derive the heart rate data, blood pressure variability data, and heart rate variability data facilitates analysis using this latter data to provide a reliable indication of the validity of the blood pressure measurement according to embodiments of the invention. For example, in operation to extract the heart rate data, heart rate variability data, and blood pressure variability data, embodiments operate to continually monitor the blood pressure pulse data for a period of time (e.g., at least 1 minute).

Figure 11A:
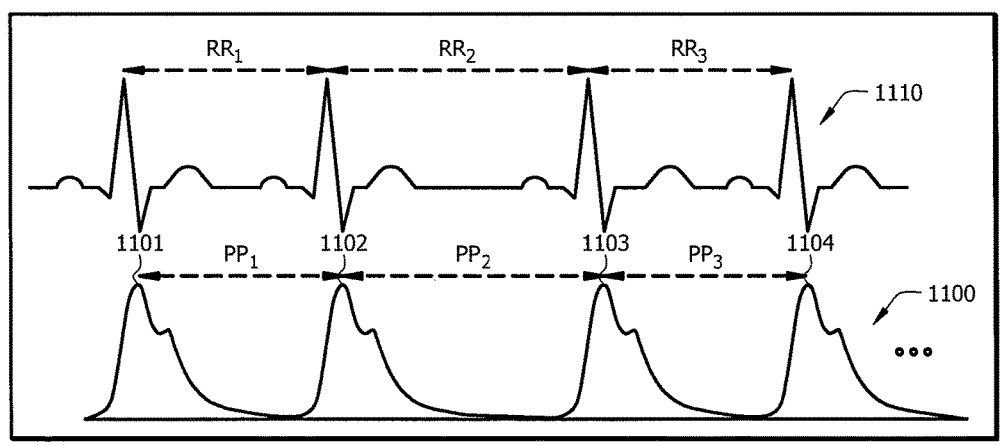
FIG. 11A-11C illustrate heart rate variability representing the variation in the beat-to-beat pulses of a subject's heart.
Figure 11B:
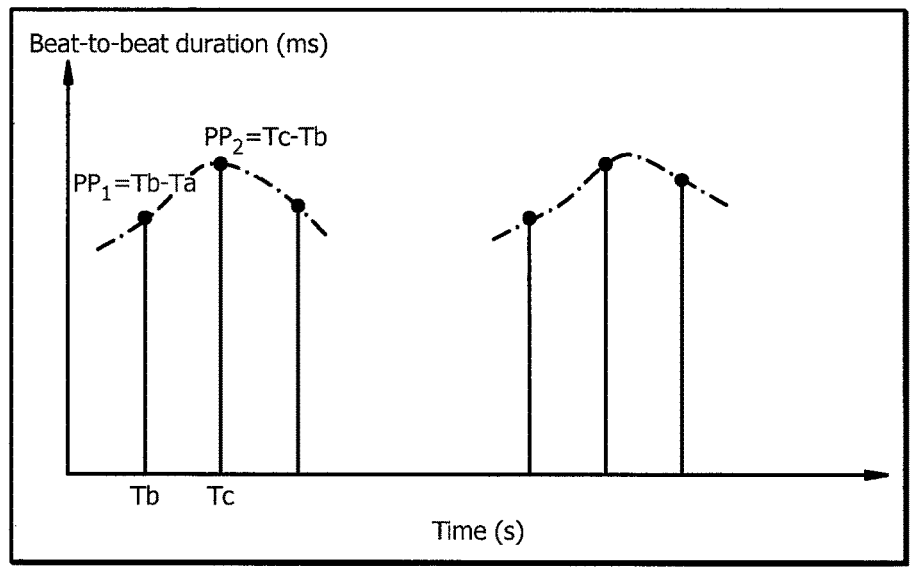
Figure 11C:
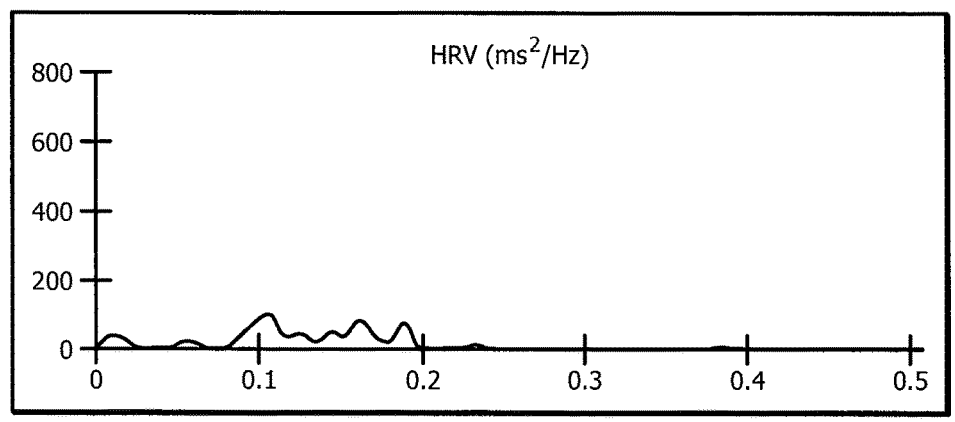

Heart rate variability data as used according to embodiments comprises a metric representing the variation in the beat-to-beat pulse rate of the subject's heart. This variability is represented by the beat-to-beat duration difference. Such variation in the beat-to-beat duration is illustrated in FIGS. 11A and 11B by $PP_1$ and $PP_2$. Signal 1100 of FIG. 11A is an example of a continuous pressure pulse signal comprising a plurality of pressure waveforms as may be provided by pressure sensor 240 and signal 1110 of FIG. 11A is a graph showing the corresponding electrical pulses of the heart beats. The heart rate variability may be determined by heart rate logic 912b of measurement logic 912 of embodiments through utilizing peak-to-peak data (e.g., peak-to-peak data provided by identification of the pressure peak of a pressure waveform of each pulse of a continuous pressure pulse signal by data feature identification logic 911). For example, $PP_1$ and $PP_2$ used in providing the heart rate variability data according to embodiments may be determined as $PP_1=Tb-Ta$ and $PP_2=Tc-Tb$, where Ta, Tb, and Tc are the times of the peaks identified by data feature identification logic 911 from the pressure pulse signal. Such heart rate variability data may be transferred from time domain (e.g., as represented in FIG. 11B) into frequency domain (e.g., as represented in FIG. 11C) by discrete Fourier transform and the total spectral power may be used as the parameter evaluating the variability. For example, for normotensive people, during rest, the total spectral power can be 675 $ms^2$/Hz, while under stress and white coat effect, his/her total spectral power may become 460 $ms^2$/Hz and 920 $ms^2$/Hz respectively. Additionally or alternatively, standard deviation from average heart rate period or transform by wavelet function may be used to generate the parameter of heart rate variability according to embodiments of the invention.

To ensure the reliability of the heart rate variability data extracted, the pressure pulse may be captured for a period of time (e.g., 3 minutes). Accordingly, operation according to embodiments ensures that the radial artery/blood vessel (e.g., artery 215 of FIG. 9) from which the pressure pulse data is collected is not occluded and that pressure sensor 240 is properly placed both in position and pressing force for providing data from which heart rate variability data may be extracted in accordance with the concepts herein. For example, in order to provide pulse peaks which accurately correspond to the actual electrical pulses of the heart beats, embodiments of measurement and validation system 910 utilize the accurate placement of sensor 240 over artery 215 from which the measurements are made. Such accurate placement of the sensor provides relatively sharp, clearly defined pressure peaks and/or troughs which each correspond to single beats of the heart. Less accurate placement of the sensor (such as by conventional placement techniques) may result in less well defined peaks and/or troughs in the sharpness (e.g., rounded or truncated peaks), making it difficult or impossible to accurately determine the peak-to-peak distances. Moreover, inaccurate placement of the sensor may result in other, potentially spurious, pressure influences (e.g., pulsations from another, nearby artery, nearby veins, muscular movement, etc.) being captured in the pressure pulse signal making it difficult or impossible to accurately determine the peak-to-peak distances.

Figure 12A:
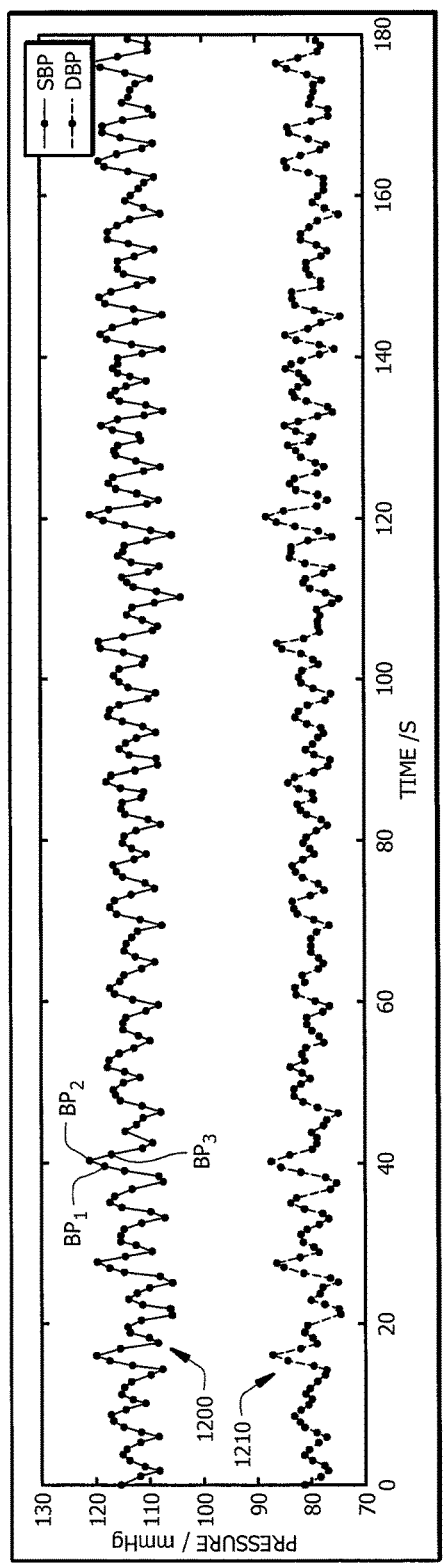
FIG. 12A-12C illustrate blood pressure variability representing the beat-to-beat variation in the subject's blood pressure.
Figure 12B:
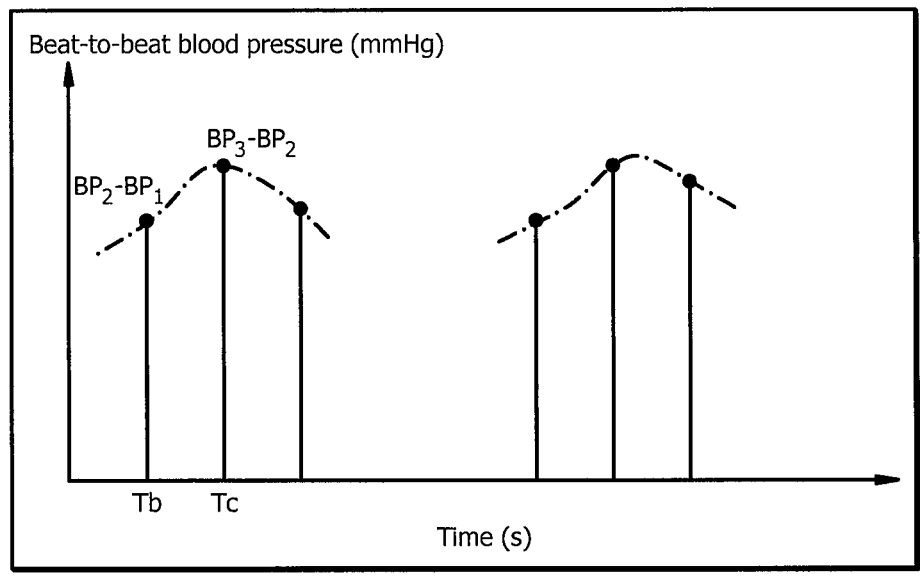
Figure 12C:
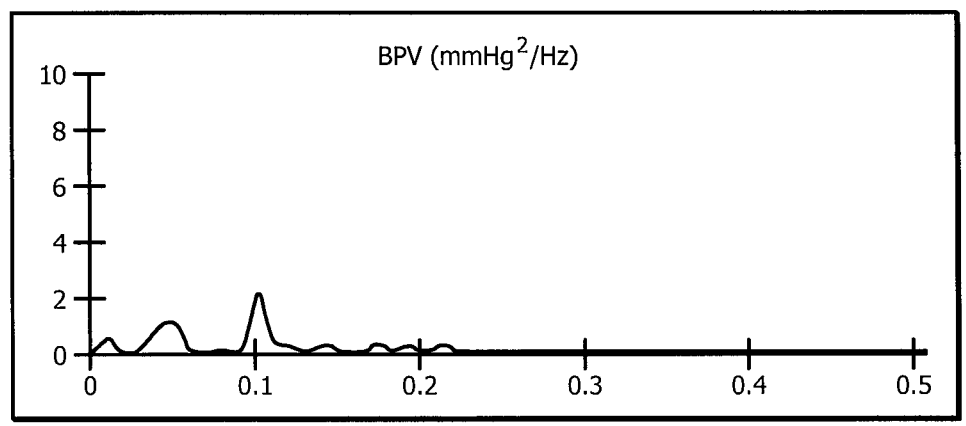

Blood pressure variability data as used according to embodiments comprises a metric representing the beat-to-beat variation in the subject's blood pressure. This variability is represented by the beat-to-beat blood pressure difference. Such variation in the beat-to-beat pressure is illustrated in FIGS. 12A and 12B. Graph 1200 of FIG. 12A is an example of the systolic blood pressure derived from a continuous pressure pulse signal comprising a plurality of pressure waveforms as may be provided by pressure sensor 240 (e.g., pressure pulse signal 1100 of FIG. 11) and graph 1210 of FIG. 12A is an example of the diastolic blood pressure derived from a continuous pressure pulse signal comprising a plurality of pressure waveforms as may be provided by pressure sensor 240. The blood pressure differences $BP_2-BP_1$ and $BP_3-BP_2$, at times Tb and Tc, as shown in FIG. 12B, show an example of beat-to-beat blood pressure differences. Such blood pressure variability may be determined by blood pressure logic 912a of measurement logic 912 of embodiments through operation to identify the pressure peak of each pulse of a continuous pressure pulse signal to identify heart beats and utilize the magnitude of the peaks to determine the blood pressure variability. The blood pressure variability data may be transferred from time domain (as represented in FIG. 12B) into frequency domain (as represented in FIG. 12C) by discrete Fourier transform and the total spectral power may be used as the parameter evaluating the variability. For example, for normotensive people, during rest, the total spectral power may be 14 mmHg$^2$/Hz, while under stress and white coat effect, his/her total spectral power may become 17 mmHg$^2$/Hz and 18.5 mmHg$^2$/Hz respectively. Additionally or alternatively, standard deviation from average beat-to-beat blood pressure or transform by wavelet function may be used to generate the parameter of blood pressure variability according to embodiments of the invention.

To ensure the reliability of the blood pressure variability data extracted, the pressure pulse may be captured for a period of time (e.g., 3 minutes). Accordingly, operation according to embodiments ensures that the radial artery/blood vessel (e.g., artery 215 of FIG. 9) from which the pressure pulse data is collected is not occluded and the pressure sensor 240 is properly placed both in position and pressing force for providing data from which blood pressure variability data may be extracted in accordance with the concepts herein. For example, in order to obtain beat-to-beat blood pressure data as may be utilized in deriving blood pressure variability, embodiments of measurement validation system 910 utilize the placement of pressure sensor 240 over artery 215 with a predetermined hold-down pressure (e.g., pressure sensor 240 is held against the subject's skin at a pressure very near the blood pressure of that subject) for making the pressure measurements. Such a hold-down pressure allows for accurate pressure measurements restricting or unacceptably impeding the flow of blood through artery 215, and thus without adversely affecting the blood pressure therein. That is, operation according to embodiments herein provides for continues collection of pressure pulse data from which blood pressure data is derived, without blocking the blood flow (e.g., as in traditional blood pressure cuff techniques), providing beat-to-beat data as used herein.

Some or all of the foregoing data may be utilized by analysis logic 913 of embodiments to identify whether the blood pressure measurement properly and accurately reflects the situation of the subject. For example, analysis logic 913 may operate to compare heart rate variability data and blood pressure variability data with baseline data for the subject (e.g., as stored in database 914) in determining the validity of the blood pressure data (e.g., determining whether the blood pressure data is or is not effected by one or more psychological influencing factors, such as the white coat effect). It should be appreciated that all of the foregoing data utilized by the analysis logic in determining the validity of the blood pressure data is derived according to the exemplary embodiment from measurements taken from the same location on the subject at the same time as the blood pressure measurement being validated (i.e., collection of the blood pressure data and the data from which the blood pressure variability data and heart rate variability data are derived are neither staggered in time nor gathered from different positions on the subject's body).

In understanding the use of data coupled in sensed time and sensed location for validating a measurement according to embodiments of the invention, it should be realized that the effect of stress may be characterized using heart rate variability measured through electrocardiogram (ECG) or photoplethysmography (PPG). However, the use of such ECG or PPG in an attempt to validate blood pressure measurements is problematic.

For example, ECG data is often not collected at the same time as the blood pressure measurement, due to the relatively complicated nature of ECG measurement techniques, the number of sensors placed on the body, etc. Although providing very accurate heart rate variability information, ECG measurement techniques cannot provide blood pressure variability information. This requires separate sensed data (e.g., collected by a different sensor at a different time and/or different location on the subject's body) for blood pressure variability information which is difficult to accurately align at a beat-to-beat level with the ECG heart rate variability information, and thus affects the accuracy and reliability of psychological influencing factor analysis. Moreover, the nature of the ECG measurement techniques and the devices used often themselves introduce a psychological influencing factor with respect to many subjects.

PPG data is likewise typically not collected at the same time as the blood pressure measurement. For example, PPG data is often collected by an optical sensor sensing from a finger of a subject, whereby when a blood pressure cuff is used for obtaining blood pressure data the blood flow to the finger at which the PPG sensor is disposed is obstructed. Thus, the PPG data is collected at a time other than when the blood pressure data is collected. Further, PPG measurement techniques provide measurement of blood flow, from which heart rate variability data may be derived. In addition to potential data accuracy issues with respect to the derived heart rate variability data, the PPG data is collected by a different sensor at a different location on the subject's body than the blood pressure data and thus may not accurately correspond with that data.

However, the blood pressure variability data and heart rate variability data of embodiments of the invention is coupled in both sensed time and sensed location with the blood pressure data. Thus, psychological influencing factors impinging upon the subject at the time of the blood pressure measurement may be accurately reflected in operation of embodiments of the present invention.

In identifying the presence of psychological influencing factors, embodiments of analysis logic 913 compares the blood pressure variability data, heart rate variability data, and heart rate data which is coupled in sensed time and sensed location with the blood pressure data being verified to baseline data for the subject. For example, baseline blood pressure variability data, heart rate variability data, and heart rate data for the subject may be stored in database 914, such as may be part of measurement and validation system 910 or accessible thereto (e.g., via a network connection). Such baseline data may be generated through collecting pressure pulse data from the subject over some period of time (e.g., a plurality of sessions over the course of several days, one or more weeks, a month, etc.) and/or in one or more settings (e.g., at the home of the subject, at the workplace for the subject, at a non-clinical venue, at a clinic without the presence of known influencing factors, etc.). The pressure pulse data collected in accordance with the foregoing may be utilized to derive exemplary blood pressure variability data, heart rate variability data, and/or heart rate data for the subject. Such exemplary data may be processed (e.g., to exclude extreme or outlier data, to determine a statistical representation, such as mean, average, weighted average, etc.) to provide baseline values for the subject. For example, embodiments of analysis logic 913 may operate to generate baseline blood pressure variability data, heart rate variability data, and heart rate data as the average of a plurality of measured instances of such metrics and store the baseline data in database 914, perhaps including one or more variance metric (e.g., one or more heart rate variability threshold, such as $T_{HRV1}$ used in determining a first psychological influencing factor (e.g., mental stress), $T_{HRV2}$ used in determining a second psychological influencing factor (e.g., white coat effect), and one or more blood pressure variability threshold, such as $T_{BPV}$ used in determining the first and second psychological influencing factor) for use therewith.

Analysis logic 913 of embodiments operates to compare a plurality of metrics for a subject to the baseline data in order to determine the presence of one or more psychological influencing factors. For example, the blood pressure variability, the heart rate variability, and the heart rate derived from pressure pulse information for a blood pressure measurement being verified may each be compared to one or more corresponding baseline values (i.e., baseline blood pressure variability, heart rate variability, and heart rate) for the subject. Analysis logic 913 may determine the presence of a mental stress factor where the heart rate variability is outside of a variance metric (e.g., $T_{HRV1}$, wherein $T_{HRV1}$ may be ±5% for example) with respect to a baseline heart rate variability for the subject (e.g., heart rate variability is higher or lower than the baseline heart rate variability by $T_{HRV1}$) and the blood pressure variability is above a variance metric (e.g., $T_{BPV}$, wherein $T_{BPV}$ may be 16-17 mmHg$^2$/Hz for example) with respect to a baseline blood pressure variability for the subject (e.g., blood pressure variability is higher than the baseline blood pressure variability by $T_{BPV}$). Additionally or alternatively, analysis logic 913 may determine the presence of a white coat effect factor where the blood pressure variability is below a variance metric (e.g., $T_{HRV2}$, wherein $T_{HRV2}$ may be 18-19 mmHg$^2$/Hz for example) and the blood pressure variability is above a variance metric (e.g., $T_{BPV}$) with respect to a baseline blood pressure variability for the subject (e.g., blood pressure variability is higher than the baseline blood pressure variability by $T_{BPV}$).

Having determined that a psychological influencing factor is or is not present, analysis logic 913 of embodiments may operate to report the data and/or conclusion (e.g., reporting the data/conclusion via a user interface of measurement validation system 910, providing a signal to output 915 for reporting the data/conclusion via a user interface of the blood pressure measurement system, etc.). Additionally or alternatively, analysis logic 913 may operate to provide control with respect to the blood pressure measurement reporting (e.g., providing a signal to output 915 to allow/suppress blood pressure measurement reporting by the blood pressure measurement system, display a valid/invalid alert flag in association with the reporting of the blood pressure measurement by the blood pressure measurement system, etc.).

Figure 13:
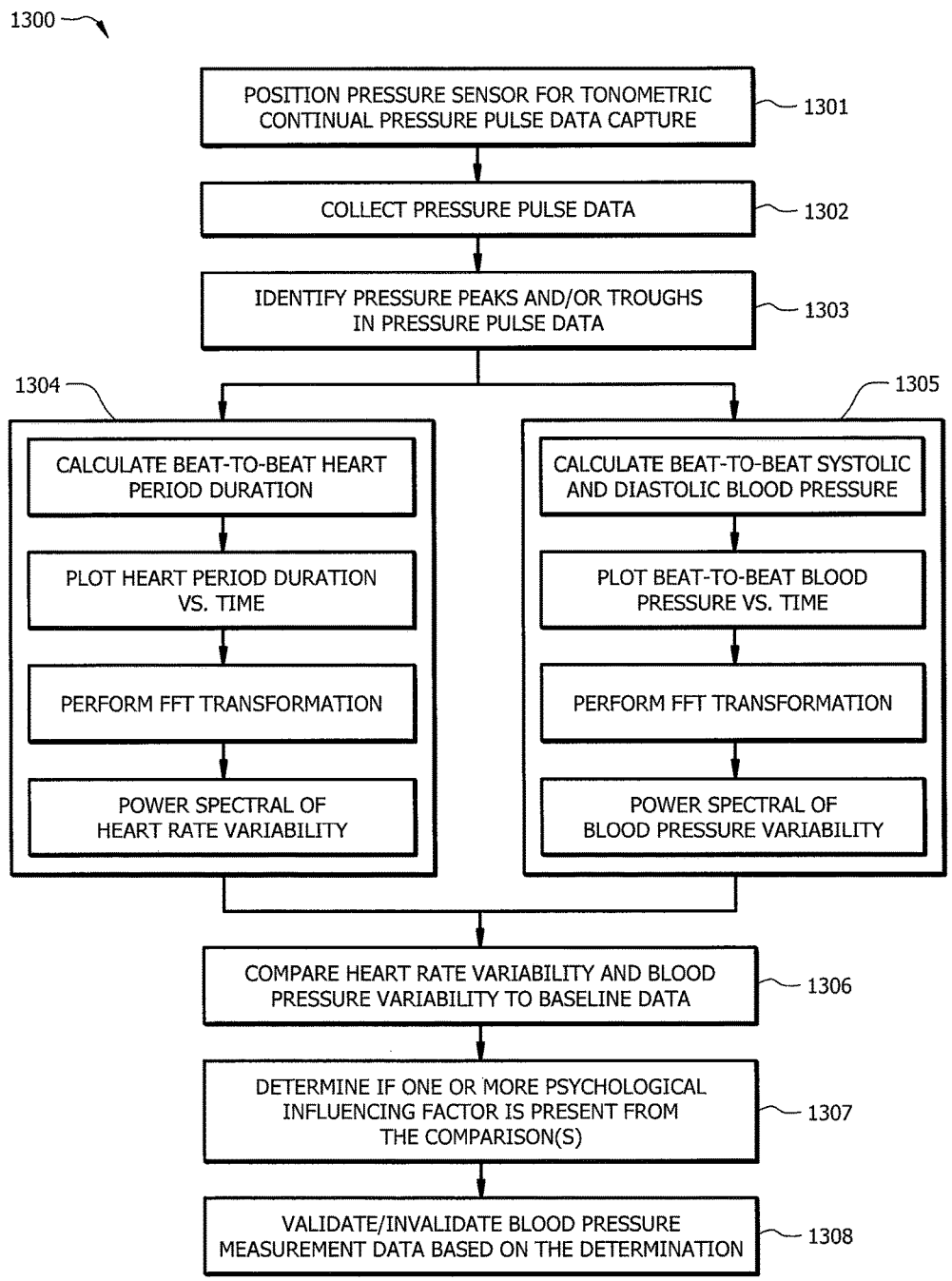
FIG. 13 shows a high level flow diagram of operation of a psychological status validation system of embodiments of the invention.

FIG. 13 shows a high level flow diagram of operation of embodiments of psychological status validation system 900 in accordance with the foregoing. At block 1301 of flow 1300 pressure sensor 240 is positioned for tonometric continual pressure pulse data capture, such as in accordance with the techniques described above. Thereafter, pressure pulse data is collected at block 1302, such as in the form of a continuous pressure pulse signal (e.g., signal 1100 of FIG. 11), for use in psychological status validation according to the concepts herein. Such a pressure pulse signal may be analyzed to identify pressure peaks and/or troughs (e.g., as described above with respect to data feature identification logic 911) at block 1303.

Using information regarding such identification of pressure peaks and/or troughs, heart rate data and heart rate variability data is extracted at block 1304 and blood pressure data and blood pressure variability data is extracted at block 1305 of the illustrated embodiment (e.g., as described with respect to measurement logic 912). For example, heart rate logic 912b of embodiments may operate to calculate the beat-to-beat heart period duration, plot the heart period duration verses time, perform a FFT transform of the plotted heart rate duration, and determine the total spectral power of the transformed heart rate variability at block 1304, as described above. Similarly, blood pressure logic 912a of embodiments may operate to calculate the beat-to-beat systolic and diastolic blood pressure, plot the beat-to-beat blood pressure verses time, perform a FFT transform of the plotted blood pressure, and determine the total spectral power of the transformed blood pressure variability at block 1305, as described above.

It should be appreciated that, although blocks 1304 and 1305 are shown as providing calculation of heart rate and heart rate variability data in parallel with calculation of blood pressure and blood pressure variability data, embodiments may operate to perform the various calculations serially, partially serially and partially in parallel, etc. For example, some or all of the operations of block 1304 may be completed prior to performing some or all of the operations of block 1305, and vice versa.

At block 1306 of the illustrated embodiment, the calculated heart rate variability and blood pressure variability is compared to baseline heart rate variability and blood pressure variability data for the subject. A determination is made regarding whether one or more psychological influencing factor (e.g., mental stress and/or white coat effect) is present from the comparison(s) of the calculated heart rate variability and blood pressure variability is compared to baseline heart rate variability and blood pressure variability data for the subject at 1306 of the illustrated embodiment. Using this determination, the illustrated embodiment operates to validate or invalidate the blood pressure measurement data at block 1307, wherein such validation or invalidation may include reporting the determination, allowing/suppressing reporting of the blood pressure measurement, etc.

Embodiments have been described above as including various functional blocks performing operations detailed herein. The various functional blocks may be implemented using processor-based systems, such as may comprise one or more general purpose processor (e.g., comprising a central processing unit (CPU) such as a PENTIUM or CORE processor available from Intel Corporation) and/or special purpose processor (e.g., an application specific integrated circuit (ASIC) or programmable gate array (PGA)) operable to provide logic defining operation as described herein. Such processors may operate under control of one or more instruction set (e.g., application program, applet, widget, firmware, software, network loadable module, etc.) to provide logic defining various operations herein. Such processor-based systems may comprise memory (e.g., random access memory (RAM), read only memory (ROM), disk memory, flash memory, optical memory, etc.), input/output apparatus (e.g., biometric sensors, keyboard, digital pointing device, display monitor, touch screen, microphone, speakers, network interface card (NIC), modem, radio, universal serial bus (USB), etc.), peripherals (e.g., printer, scanner, etc.) to facilitate performing operations described herein.

The present invention may be embodied in other specific forms without departing from the spirit or essential characteristics thereof. The present embodiment is therefore to be considered in all respects as illustrative and not restrictive. The scope of the invention is indicated by the appended claims rather than by the foregoing description, and all changes that come within the meaning and range of equivalency of the claims are therefore intended to be embraced therein.

What is claimed is:

1. A system for validating a psychological status with respect to a blood pressure measurement, the system comprising:

a pressure sensor platform adapted for measuring continual pressure pulse of a subject and providing pressure pulse data for the subject from the measured continual pressure pulse, wherein the pressure pulse data comprises data for a plurality of pressure waveforms associated with beat-to-beat blood pressure values of the subject;

data feature identification logic configured to identify peaks and troughs of the plurality of pressure waveforms;

measurement logic configured to derive a blood pressure measurement for the subject from the pressure pulse data and to derive heart rate variability data and blood pressure variability data from the pressure pulse data using the identified peaks and troughs of the plurality of pressure waveforms; and analysis logic configured to analyze the heart rate variability data and blood pressure variability data and determine if one or more psychological influencing factors is present with respect to the subject, wherein the analysis logic provides information regarding validity of the blood pressure measurement based on the determination if one or more psychological influencing factors is present and outputs a signal indicating invalidity of the blood pressure measurement when the analysis logic determines that the one or more psychological influencing factors is present and indicating validity of the blood pressure measurement when the analysis logic determines that the one or more psychological influencing factors is not present; and wherein the analysis logic is configured to trigger one or more additional measurements for deriving an additional blood pressure measurement for the subject in response to the signal indicating invalidity of the blood pressure measurement and to cause the blood pressure measurement to be recorded in response to the signal indicating validity of the blood pressure measurement.

2. The system of claim 1, wherein the pressure sensor platform comprises:

a tonometric pressure sensor, wherein the tonometric pressure sensor is applied to a surface of the subject with a pressure approximating a blood pressure for the continual pressure pulse measurement.

3. The system of claim 2, wherein the pressure sensor platform comprises:

an optical sensor, wherein the tonometric pressure sensor is applied to the surface of the subject in juxtaposition with a radial artery of the subject as determined using the optical sensor.

4. The system of claim 1, wherein the measurement logic derives the heart rate variability data and the blood pressure variability data from the pressure pulse data based on differences between data of the pressure pulse data for adjacent heart beats of the subject.

5. The system of claim 1, wherein the measurement logic further derives a heart rate for the subject from the pressure pulse data.

6. The system of claim 5, wherein the pressure pulse data is collected for a predetermined period of time, wherein the predetermined period of time is of at least 1 minute in duration.

7. The system of claim 1, further comprising:

a database of baseline heart rate variability data and blood pressure variability data for the subject, wherein the analysis logic operates to compare the derived heart rate variability data and blood pressure variability data for the subject with the baseline heart rate variability data and blood pressure variability data for the subject to determine if one or more psychological influencing factor is present with respect to the subject.

8. The system of claim 7, wherein the analysis logic operates to determine a mental stress is present with respect to the subject if the derived heart rate variability data is below the baseline heart rate variability data by a second heart rate variability variance metric ($T_{HRV2}$) and the derived blood pressure variability data is above the baseline blood pressure variability data by a blood pressure variability variance metric ($T_{BPV}$), wherein the mental stress is a psychological influencing factor of the one or more psychological influencing factors.

9. A method for validating a psychological status with respect to a blood pressure measurement, the method comprising:

providing pressure pulse data from a measured continual pressure pulse of a subject, wherein the pressure pulse data comprises data for a plurality of pressure waveforms associated with beat-to-beat blood pressure values of the subject;

identifying peaks and troughs of the plurality of pressure waveforms;

calculating a blood pressure measurement for the subject from the pressure pulse data;

calculating heart rate variability data from the pressure pulse data using the identified peaks and troughs;

calculating blood pressure variability data from the pressure pulse data using the identified peaks and troughs;

analyzing the calculated heart rate variability data and blood pressure variability data;

determining if one or more psychological influencing factors is present with respect to the subject based on the analyzing;

providing a signal regarding validity of the blood pressure measurement based on the determination if one or more psychological influencing factors is present, wherein the signal indicates invalidity of the blood pressure measurement when the one or more psychological influencing factors is determined to be present with respect to the subject and the signal indicates validity of the blood pressure measurement when the one or more psychological influencing factors is determined not to be present with respect to the subject; and triggering one or more additional pressure pulse measurements for calculating an additional blood pressure measurement for the subject in response to the signal indicating invalidity of the blood pressure measurement and recording the blood pressure measurement in response to the signal indicating validity of the blood pressure measurement.

10. The method of claim 9, further comprising:

applying a tonometric pressure sensor to a surface of the subject with a pressure approximating a blood pressure, wherein the measured continual pressure pulse of the subject is measured using the tonometric pressure sensor applied to the surface of the subject with the pressure approximating the blood pressure.

11. The method of claim 10, further comprising:

locating a radial artery of the subject using an optical sensor, wherein the tonometric pressure sensor is applied to the surface of the subject in juxtaposition with the radial artery at a location determined using the optical sensor.

12. The method of claim 9, wherein the calculating heart rate variability data from the pressure pulse data is based on differences between data of the pressure pulse data for adjacent heart beats of the subject.

13. The method of claim 9, wherein the calculating blood pressure variability data from the pressure pulse data is based on differences between data of the pressure pulse data for adjacent heart beats of the subject.

14. The method of claim 9, further comprising:
calculating a heart rate for the subject from the pressure pulse data.

15. The method of claim 9, wherein the pressure pulse data is collected for a predetermined period of time, wherein the predetermined period of time is of at least 1 minute in duration.

16. The method of claim 9, further comprising:
comparing the calculated heart rate variability data and blood pressure variability data for the subject with baseline heart rate variability data and blood pressure variability data for the subject, wherein the determining if one or more psychological influencing factor is present with respect to the subject is based on the comparing.

17. The method of claim 16, wherein the determining if one or more psychological influencing factor is present with respect to the subject comprises:
determining a mental stress is present with respect to the subject if the calculated heart rate variability data is below the baseline heart rate variability data by a heart rate variability variance metric and the calculated blood pressure variability data is above the baseline blood pressure variability data by a blood pressure variability variance metric, wherein the mental stress is a psychological influencing factor of the one or more psychological influencing factors.

18. A system for validating a psychological status with respect to a blood pressure measurement, the system comprising:
a pressure sensor platform adapted for measuring continual pressure pulse of a subject and providing pressure pulse data for the subject from the measured continual pressure pulse, wherein the pressure pulse data comprises data for a plurality of pressure waveforms associated with beat-to-beat blood pressure values of the subject;
data feature identification logic configured to identify peaks and troughs of the plurality of pressure waveforms;
measurement logic configured to calculate heart rate variability data and blood pressure variability data from beat-to-beat differences in data of the pressure pulse data, wherein the blood pressure measurement is also calculated from the pressure pulse data using the identified peaks and troughs of the plurality of pressure waveforms; and
analysis logic configured to analyze the calculated heart rate variability data and blood pressure variability data and determine if one or more psychological influencing factors is present with respect to the subject, wherein the analysis logic provides a signal regarding validity of the blood pressure measurement based on the determination if one or more psychological influencing factors is present, wherein the signal indicates invalidity of the blood pressure measurement when the one or more psychological influencing factors is determined to be present with respect to the subject and the signal indicates validity of the blood pressure measurement when the one or more psychological influencing factors is determined not to be present with respect to the subject; and
wherein the analysis logic is configured to trigger one or more additional measurements for calculating an additional blood pressure measurement for the subject in response to the signal indicating invalidity of the blood pressure measurement and to cause the blood pressure measurement to be recorded in response to the signal indicating validity of the blood pressure measurement.

19. The system of claim 18, wherein the pressure sensor platform comprises:
a tonometric pressure sensor, wherein the tonometric pressure sensor is applied to a surface of the subject with a pressure approximating a blood pressure for the continual pressure pulse measurement, wherein the pressure sensor platform comprises:
an optical sensor, wherein the tonometric pressure sensor is applied to the surface of the subject in juxtaposition with a radial artery of the subject as determined using the optical sensor.

20. The system of claim 18, wherein the measurement logic further derives a heart rate for the subject from the pressure pulse data, wherein the blood pressure measurement is calculated from the pressure pulse data.

21. The system of claim 18, wherein the analysis logic operates to determine a mental stress is present with respect to the subject if the calculated heart rate variability data is below a baseline heart rate variability data by a heart rate variability variance metric and the calculated blood pressure variability data is above a baseline blood pressure variability data by a blood pressure variability variance metric, wherein the mental stress is a psychological influencing factor of the one or more psychological influencing factors.

* * * * *

UNITED STATES PATENT AND TRADEMARK OFFICE
CERTIFICATE OF CORRECTION

PATENT NO. : 10,105,089 B2
APPLICATION NO. : 14/933647
DATED : October 23, 2018
INVENTOR(S) : Leung et al.

Page 1 of 1

It is certified that error appears in the above-identified patent and that said Letters Patent is hereby corrected as shown below:

In the Specification

Column 10, Line 19, delete "t342" and replace with --t3-t2--.

Signed and Sealed this
Twenty-second Day of January, 2019

Andrei Iancu
*Director of the United States Patent and Trademark Office*